(12) United States Patent
Takeda et al.

(10) Patent No.: US 12,736,551 B2
(45) Date of Patent: Sep. 15, 2026

(54) CELL PICKING DEVICE

(71) Applicant: SHIMADZU CORPORATION, Kyoto (JP)

(72) Inventors: Akari Takeda, Kyoto (JP); Yoshitake Yamamoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 1015 days.

(21) Appl. No.: 17/626,545

(22) PCT Filed: Jul. 26, 2019

(86) PCT No.: PCT/JP2019/029515
§ 371 (c)(1),
(2) Date: Jan. 12, 2022

(87) PCT Pub. No.: WO2021/019625
PCT Pub. Date: Feb. 4, 2021

(65) Prior Publication Data

US 2022/0268794 A1 Aug. 25, 2022

(51) Int. Cl.
*G01N 35/00* (2006.01)
*C12M 1/00* (2006.01)
(Continued)

(52) U.S. Cl.
CPC ......... *G01N 35/0099* (2013.01); *C12M 23/50* (2013.01); *C12M 33/04* (2013.01); *C12M 41/46* (2013.01); *C12M 41/48* (2013.01)

(58) Field of Classification Search
CPC combination set(s) only.
See application file for complete search history.

(56) References Cited

U.S. PATENT DOCUMENTS 6,694,197 B1 2/2004 Hatcher et al.
9,068,953 B2 6/2015 Silbert et al.
(Continued)

FOREIGN PATENT DOCUMENTS

CN 109844090 A 6/2019
EP 1909108 A2 * 4/2008 ........... G01N 35/025
(Continued)

OTHER PUBLICATIONS

Office Action in corresponding Chinese Patent Application No. 2019800982684 dated Dec. 11, 2023, with English machine translation.

(Continued)

*Primary Examiner* — Jyoti Mutreja
*Assistant Examiner* — Velvet Elizabeth Heron
(74) *Attorney, Agent, or Firm* — Renner, Otto, Boisselle & Sklar, LLP

(57) ABSTRACT

A cell picking device includes a supporter that supports a rack having a plurality of holes for holding a plurality of pipette tips, a sucker used to suck a sample, a driver that moves the sucker in an up-and-down direction and moves the sucker and the supporter relative to each other in a horizontal direction, and a controller that controls the driver such that, any pipette tip out of the plurality of pipette tips held by the rack is attached to the sucker by movement of the sucker in the up-and-down direction and the sucker is moved to a position outwardly of the rack by movement of the sucker and the supporter relative to each other.

4 Claims, 18 Drawing Sheets

(51) Int. Cl.

| | |
|---|---|
| ***C12M 1/26*** | (2006.01) |
| ***C12M 1/34*** | (2006.01) |
| ***C12M 1/36*** | (2006.01) |

(56) References Cited

U.S. PATENT DOCUMENTS

| | | | |
|---|---|---|---|
| 10,449,534 | B2 | 10/2019 | Berberich et al. |
| 2007/0072168 | A1 | 3/2007 | Ryle |
| 2015/0037213 | A1 | 2/2015 | Silbert et al. |
| 2016/0169775 | A1 | 6/2016 | Kei |
| 2020/0040295 | A1 | 2/2020 | Ito |

FOREIGN PATENT DOCUMENTS

| | | | | | |
|---|---|---|---|---|---|
| JP | 2007-020422 | A | | 2/2007 | |
| JP | 2016-112012 | A | | 6/2016 | |
| JP | 2019041691 | A | * | 3/2019 | |
| WO | WO-2018013346 | A1 | * | 1/2018 | .............. B25J 9/026 |
| WO | WO-2018191534 | A1 | * | 10/2018 | |
| WO | 2019/018152 | A1 | | 1/2019 | |

OTHER PUBLICATIONS

International Search Report for corresponding Application No. PCT/JP2019/029515, mailed Oct. 21, 2019.

Written Opinion for corresponding Application No. PCT/JP2019/029515, mailed Oct. 21, 2019 (English machine translation).

Final Office Action issued in related U.S. Appl. No. 17/531,065 dated Jul. 30, 2024.

Office Action in related U.S. Appl. No. 17/531,065 dated Oct. 23, 2023.

Roselle et al. 2016 "Mitigation of microtiter plate positioning effects using a block randomization scheme." Anal Bioanal Chem 408, 3969-3979 (11 pages total); doi: 10.1007/s00216-016-9469-0; (Year: 2016).

Office Action in related CN Application No. 202111399747.5 dated Jan. 4, 2024, with English machine translation.

Office Action in related Japanese Application No. 2020-196185 dated Mar. 26, 2024, with English machine translation.

Office Action for corresponding Japanese Patent Application No. 2020-196185 dated Nov. 5, 2024, with English machine translation.

Office Action in corresponding Chinese Patent Application No. 201980098268.4 dated Mar. 13, 2024, with English machine translation.

Office Action for corresponding Chinese Patent Application No. 202111399747.5 dated Aug. 30, 2024, with English machine translation.

Office Action issued in the related U.S. Appl. No. 17/531,065 dated Dec. 17, 2024.

Final Office Action issued in related U.S. Appl. No. 17/531,065 dated Jun. 30, 2025.

Decision of Refusal in corresponding Chinese Patent Application No. 202111399747.5 dated Jan. 22, 2025, with English machine translation.

Office Action issued in related U.S. Appl. No. 17/531,065 dated Jun. Nov. 18, 2025.

Office Action issued in related U.S. Appl. No. 17/531,065 dated May 4, 2026.

* cited by examiner

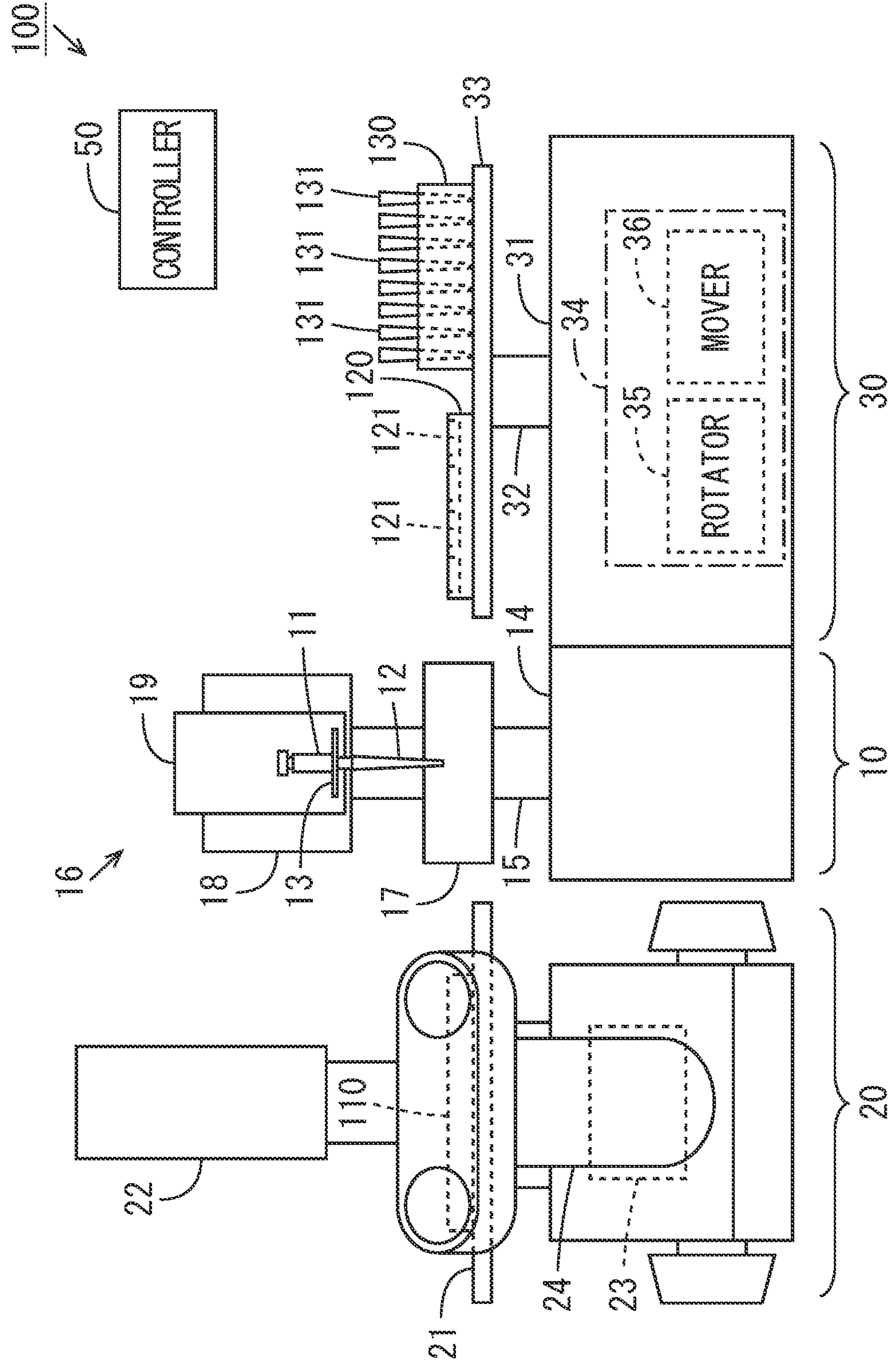
F I G. 1

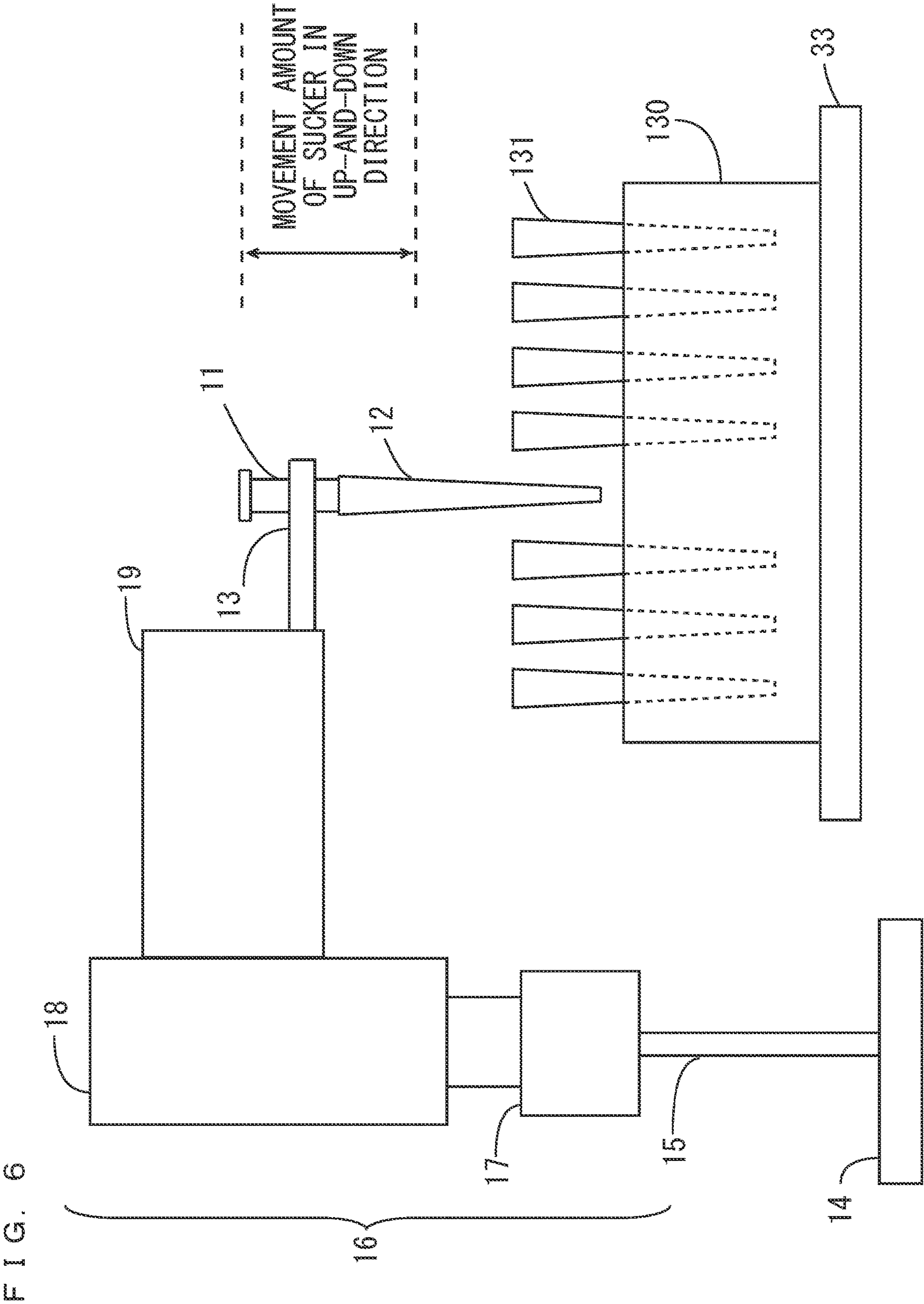
F I G. 6
MOVEMENT AMOUNT
OF SUCKER IN
UP-AND-DOWN
DIRECTION
11
12
13
14
15
16
17
18
19
33
130
131

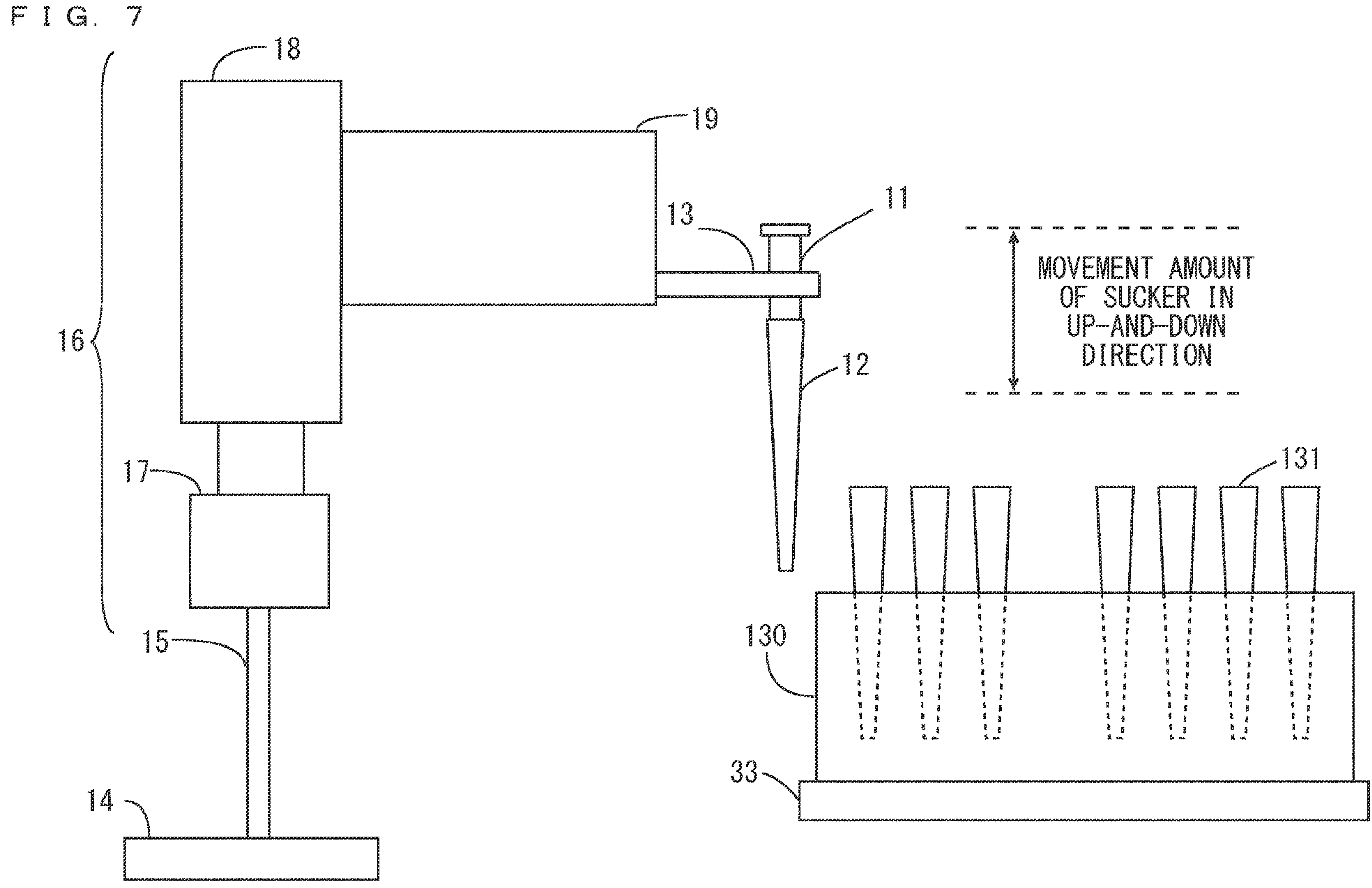
F I G. 7
18
19
13
11
MOVEMENT AMOUNT OF SUCKER IN UP-AND-DOWN DIRECTION
16
12
17
131
130
15
33
14

11
12
13
19
131
130
33
18
17
15
14
16

MOVEMENT AMOUNT
OF SUCKER IN
UP-AND-DOWN
DIRECTION
33
130
131
11
12
19
13
18
17
15
14
16

MOVEMENT AMOUNT OF SUCKER IN UP-AND-DOWN DIRECTION
11
12
13
14
15
16
17
18
19
33
130
131

100
50
CONTROLLER
2
120
121
121
121
33
31
130
131
131
131
131
131
11
13
14
32
34
35
36
ROTATOR
MOVER
30
19
18
17
16
15
10
22
110
21
24
23
20
x
z

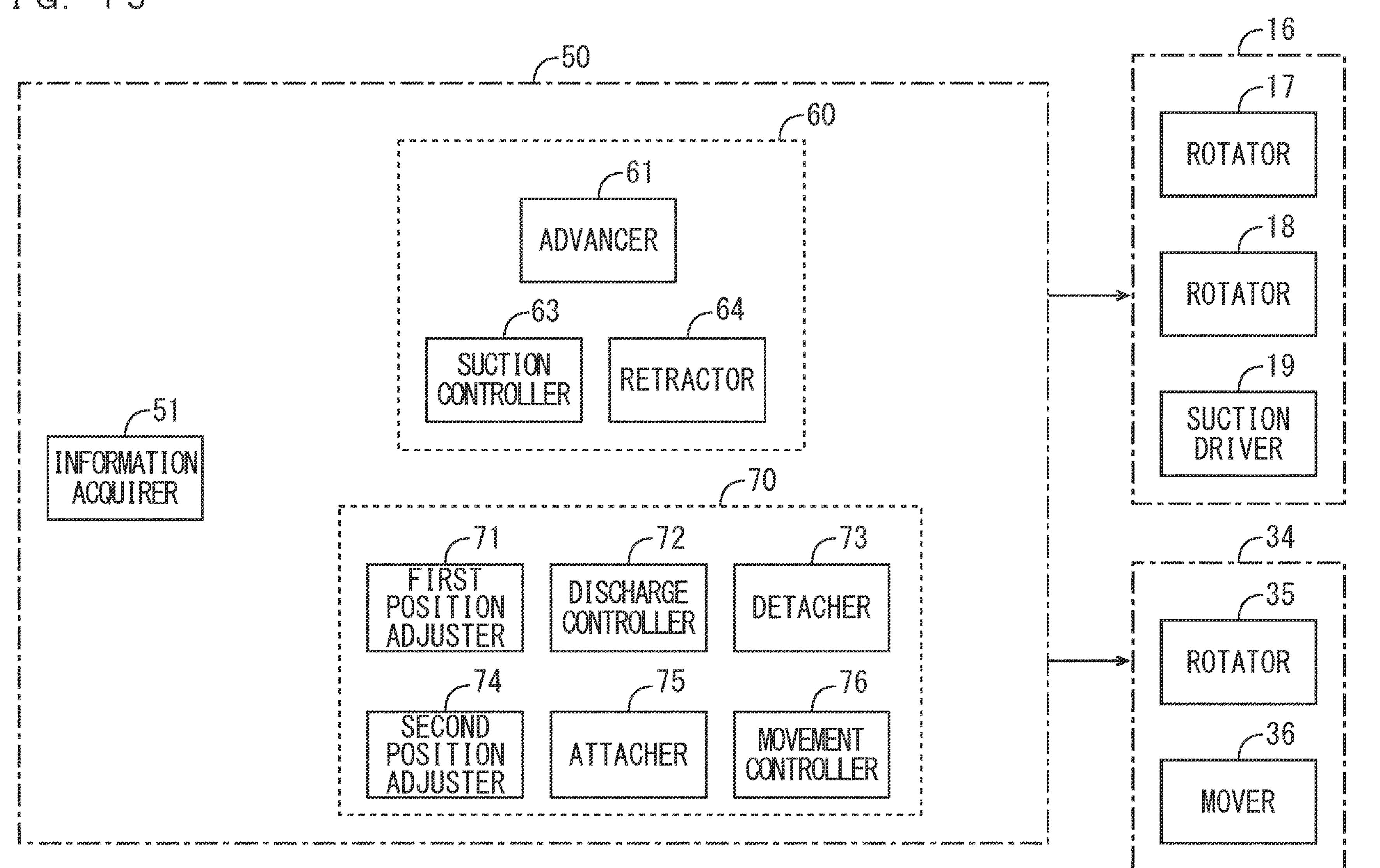
F I G. 15
50
60
61
ADVANCER
63
SUCTION CONTROLLER
64
RETRACTOR
51
INFORMATION ACQUIRER
70
71
FIRST POSITION ADJUSTER
72
DISCHARGE CONTROLLER
73
DETACHER
74
SECOND POSITION ADJUSTER
75
ATTACHER
76
MOVEMENT CONTROLLER
16
17
ROTATOR
18
ROTATOR
19
SUCTION DRIVER
34
35
ROTATOR
36
MOVER F I G. 16
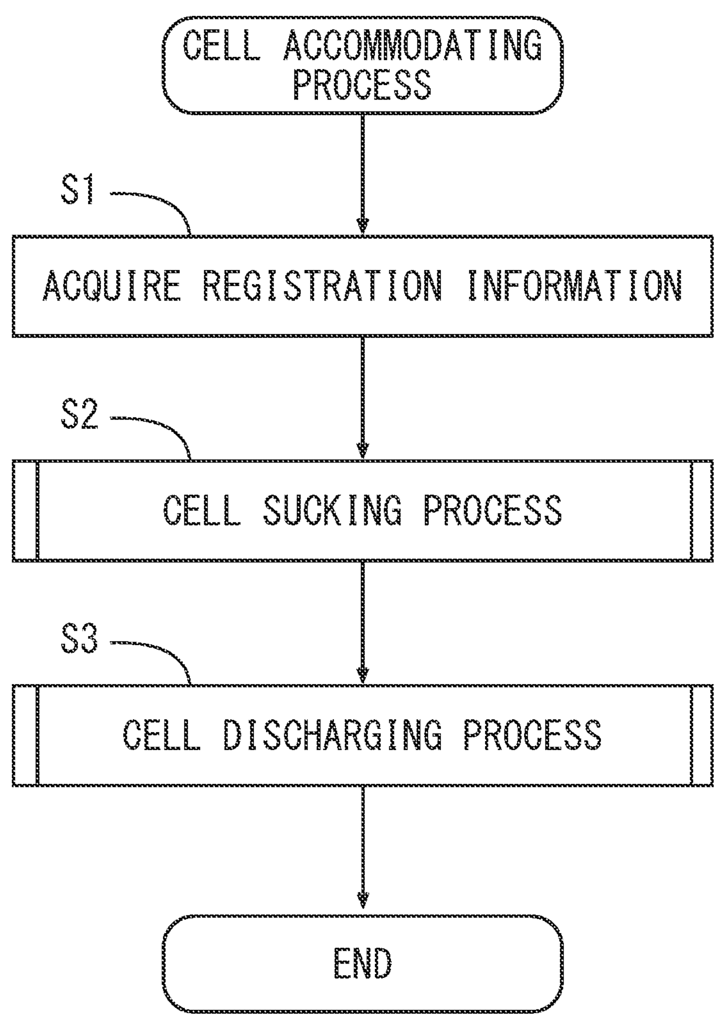

F I G. 1 7
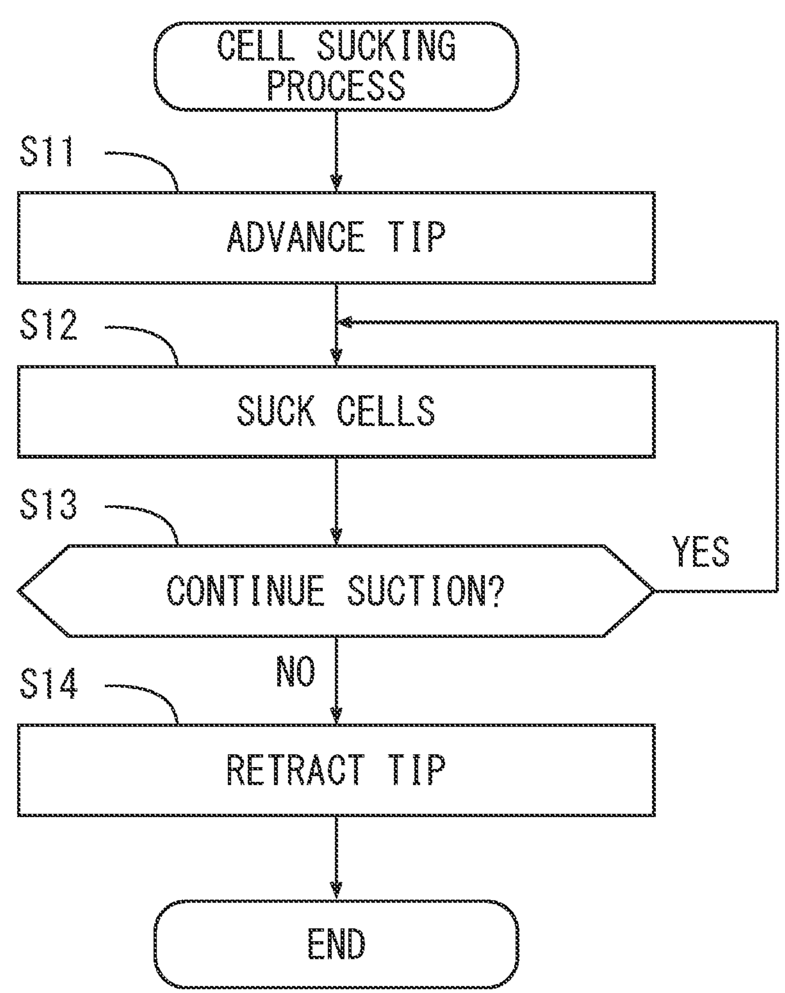

CELL PICKING DEVICE

TECHNICAL FIELD

The present invention relates to a cell picking device.

BACKGROUND ART

In a case where specific cells are to be sucked from a container such as a cell culture container, a worker sucks the cells manually using a suction tool such as a pipette while checking the position of the subject cells with a microscope. Further, since such work requires a skill, a cell-sucking system that assists cell-sucking work has been suggested for an unskilled worker (see Patent Document 1, for example).

In the cell-sucking system described in Patent Document 1, a tubular tip for sucking cells contained in a container is attached to a sucker. The end of the tip is detected optically by a detector, and the sucker is moved three-dimensionally by a transporter such that the end of the tip is guided into specific cells based on its detection result.

[Patent Document 1] JP 2016-112012 A

SUMMARY OF INVENTION

Technical Problem

Generally, a rack holding a plurality of pipette tips for replacement is arranged in the vicinity of the sucker. When a pipette tip is attached to the sucker, the sucker is moved to a position above any pipette tip out of the plurality of pipette tips held by the rack. In this state, the sucker is lifted and moved from above the rack to a position outwardly of the rack.

In a case where the sucker can be lifted sufficiently, the pipette tip attached to the sucker does not collide with another pipette tip held by the rack. However, the movement amount of the sucker in the up-and-down direction may be limited for prevention of a driver of the sucker from interfering with another constituent element of the cell picking device. In such a case, because the sucker cannot be lifted sufficiently, the pipette tip attached to the sucker may collide with another pipette tip held by the rack.

An object of the present invention is to provide a cell picking device that can prevent collision of a pipette tip.

Solution to Problem

An aspect according to the present invention relates to a cell picking device that includes a supporter that supports a rack having a plurality of holes for holding a plurality of pipette tips, a sucker used to suck a sample, a driver that moves the sucker in an up-and-down direction and moves the sucker and the supporter relative to each other in a horizontal direction, and a controller that controls the driver such that, any pipette tip out of the plurality of pipette tips held by the rack is attached to the sucker by movement of the sucker in the up-and-down direction and the sucker is moved to a position outwardly of the rack by movement of the sucker and the supporter relative to each other, wherein the controller controls the driver such that the sucker moves along a region between the plurality of holes and above the region between the plurality of holes of the rack to a position outwardly of the rack from above the rack with a lower end of a pipette tip attached to the sucker located farther downwardly than an upper end of another pipette tip held by the rack.

Advantageous Effects of Invention

With the present invention, although the lower end of a pipette tip attached to a sucker is located farther downwardly than the upper end of another pipette tip held by a rack, collision of the pipette tip can be prevented.

BRIEF DESCRIPTION OF THE DRAWINGS

FIG. 1 is a schematic diagram showing the configuration of a cell picking device according to one embodiment of the present invention.

FIG. 6 is a diagram for explaining the attachment of the tip to the sucker and the movement of the sucker.

FIG. 7 is a diagram for explaining the attachment of the tip to the sucker and the movement of the sucker.

FIG. 15 is a diagram showing the configuration of a controller of FIG. 1.

FIG. 16 is a flowchart showing one example of the algorithm of a cell accommodating process executed by a controller.

FIG. 17 is a flowchart showing one example of the algorithm of a cell sucking process of FIG. 16 executed by a suction processor.

DESCRIPTION OF EMBODIMENTS

(1) Configuration of Cell Picking Device

Figure 2:
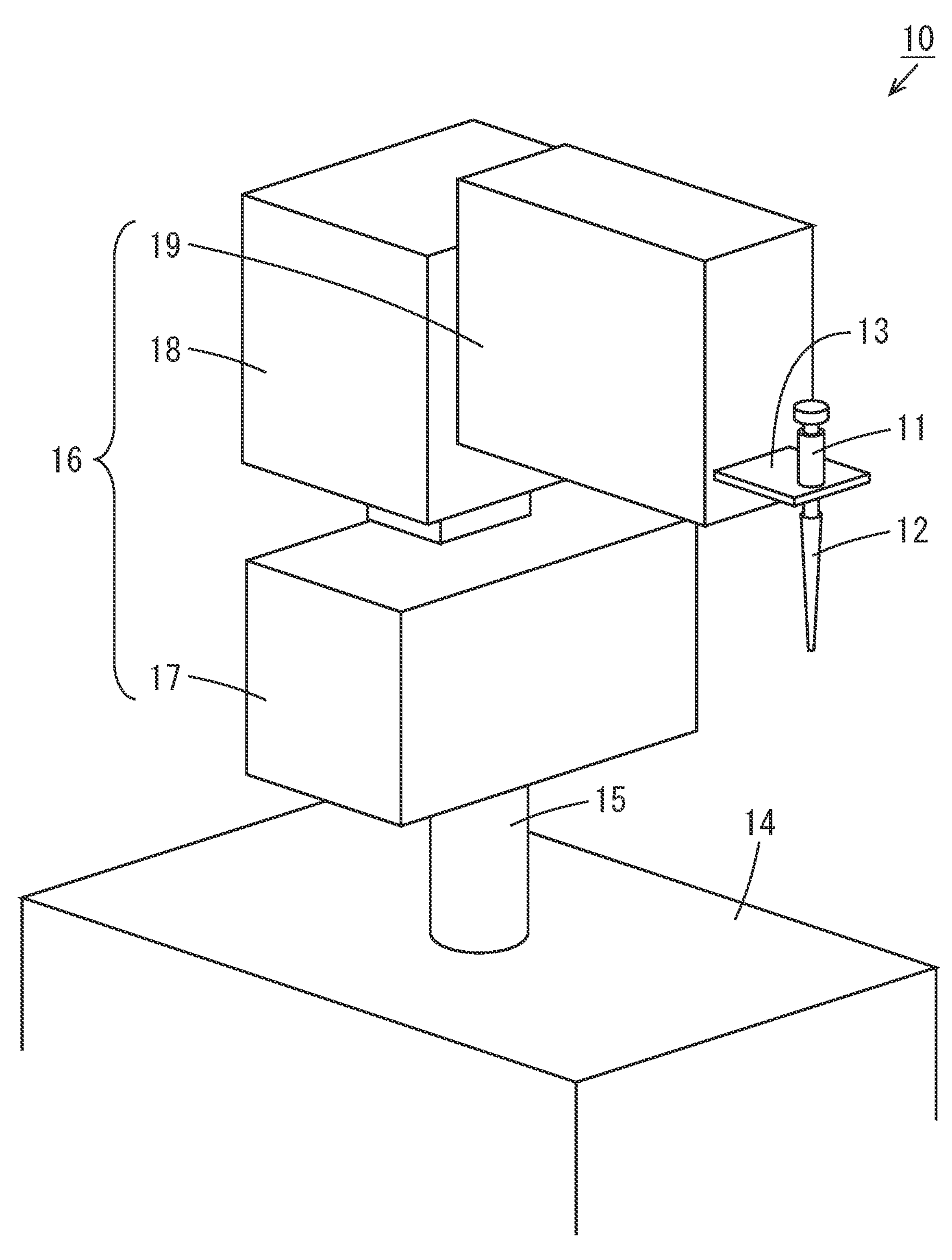
FIG. 2 is a schematic diagram showing the configuration of a suction device of FIG. 1.

A cell picking device according to embodiments of the present invention will be described below in detail with reference to the drawings. FIG. 1 is a schematic diagram showing the configuration of the cell picking device according to one embodiment of the present invention. As shown in FIG. 1, the cell picking device 100 includes a suction device 10, an observation device 20, a plate changer 30 and a controller 50. Further, the cell picking device 100 is provided with a sample container 110, a culture plate 120 and a rack 130.

The sample container 110 is a petri plate, for example, and accommodates a sample including cells. The culture plate 120 is a multi-well plate in which a plurality of wells 121 are arranged and used for culturing of cells. The rack 130 holds a plurality of replacement pipette tips 131 (hereinafter simply referred to as replacement tips 131.) In the present example, 24 wells 121 are arranged in 4 rows by 6 columns in the culture plate 120. Further, 96 replacement tips 131 are held while being arranged in 8 rows by 12 columns in the rack 130.

The suction device 10 includes a pipette-shape sucker 11. Any replacement tip 131 held by the rack 130 is attached to the end of the sucker 11 (hereinafter, a replacement tip 131 attached to the sucker 11 is simply referred to as a tip 12.) The suction device 10 sucks cells in the sample container 110 through the tip 12 and discharges (seeds) the cells into any well 121 of the culture plate 120. Thereafter, a similar operation is repeated using a new replacement tip 131 and a new well 121. Details of the configuration and operation of the suction device 10 will be described below.

The observation device 20 includes a stage 21, an illuminator 22, an imager 23 and a microscope 24 and is arranged to be adjacent to the suction device 10. The sample container 110 is placed on the stage 21. The illuminator 22 is arranged above the stage 21. The illuminator 22 includes a light source such as a light emitting diode, for example, and illuminates the sample container 110 placed on the stage 21. The stage 21 is translucent. Alternatively, an opening through which light from the illuminator 22 passes downwardly may be formed in the stage 21.

The imager 23 is arranged below the stage 21. The imager 23 includes a plurality of lenses, a camera and so on, and picks up an image while magnifying a sample in the sample container 110 illuminated by the illuminator 22. The microscope 24 includes an eyepiece, a lens-barrel, an objective lens, etc., and is used by a user when a sample in the sample container 110 placed on the stage 21 is magnified for observation.

The plate changer 30 is an optional device arranged to be opposite to the observation device 20 with the suction device 10 provided therebetween and is configured to be attachable to and detachable from the suction device 10. The plate changer 30 includes a base 31, a vertical shaft 32, a supporter 33 and a driver 34. The vertical shaft 32 is provided to extend in an up-and-down direction in the base 31. An upper portion of the vertical shaft 32 projects from the base 31. The supporter 33 is a plate member having a disc shape, for example, and is attached to the upper end of the vertical shaft 32 in a horizontal attitude. The culture plate 120 and the rack 130 are supported by the supporter 33.

The driver 34 includes a rotator 35 and a mover 36 and is connected to the supporter 33 through the vertical shaft 32 in the base 31. The rotator 35 includes an electric motor, for example, and rotates the supporter 33 in a horizontal plane. Thus, the culture plate 120 and the rack 130 supported by the supporter 33 are selectively moved to the vicinity of the suction device 10.

Specifically, when the suction device 10 discharges cells into any well 121, the culture plate 120 is moved to the vicinity of the suction device 10. On the other hand, when any replacement tip 131 is attached to the sucker 11, the rack 130 is moved to the vicinity of the suction device 10. With this configuration, an increase in moving range of the supporter 33 is prevented.

The mover 36 includes a stepping motor, for example, and moves the supporter 33 in parallel with a horizontal plane. Specifically, the mover 36 moves any well 121 of the culture plate 120 or any replacement tip 131 in the rack 130 to a position accessible by the sucker 11 (below the sucker 11, for example). Thus, cells can be discharged from the suction device 10 into a well 121, or a replacement tip 131 can be attached to the sucker 11.

The controller 50 includes a personal computer, for example, and includes a CPU (Central Processing Unit), a memory and so on. Alternatively, the controller 50 may be a microcomputer provided in each of the suction device 10 and the plate changer 30. The controller 50 controls the operations of the suction device 10 and the plate changer 30.

(2) Configuration of Suction Device

FIG. 2 is a schematic diagram showing the configuration of the suction device 10 of FIG. 1. As shown in FIG. 2, the suction device 10 includes the sucker 11, a tip 12, a holder 13, a base 14, a vertical shaft 15 and a driver 16. The driver 16 includes rotators 17, 18 and a suction driver 19. The holder 13 holds the sucker 11 at the suction driver 19. The vertical shaft 15 is provided on the upper surface of the base 14 to extend in the up-and-down direction.

The rotator 17 includes an electric motor, for example, and is attached to the upper end of the vertical shaft 15 to be rotatable in a horizontal plane. The rotator 18 includes an electric motor, for example, and is attached to the rotator 17 to be rotatable in a vertical plane. The rotator 17 and the rotator 18 may be constituted by a single electric motor, etc. which is rotatable in the horizontal plane and the vertical plane.

The suction driver 19 includes a stepping motor, for example, and is attached to the rotator 18 to be advanceable and retreatable in a predetermined direction (an up-and-down direction in a case where the rotator 18 is not rotating in the vertical plane). Further, the suction driver 19 includes a suction mechanism and is configured to be capable of sucking and discharging cells using the sucker 11. Further, the suction driver 19 includes a tip detachment mechanism and is configured to be capable of detaching the tip 12 from the end of the sucker 11.

(3) Attachment and Movement of Tip

Figure 3:
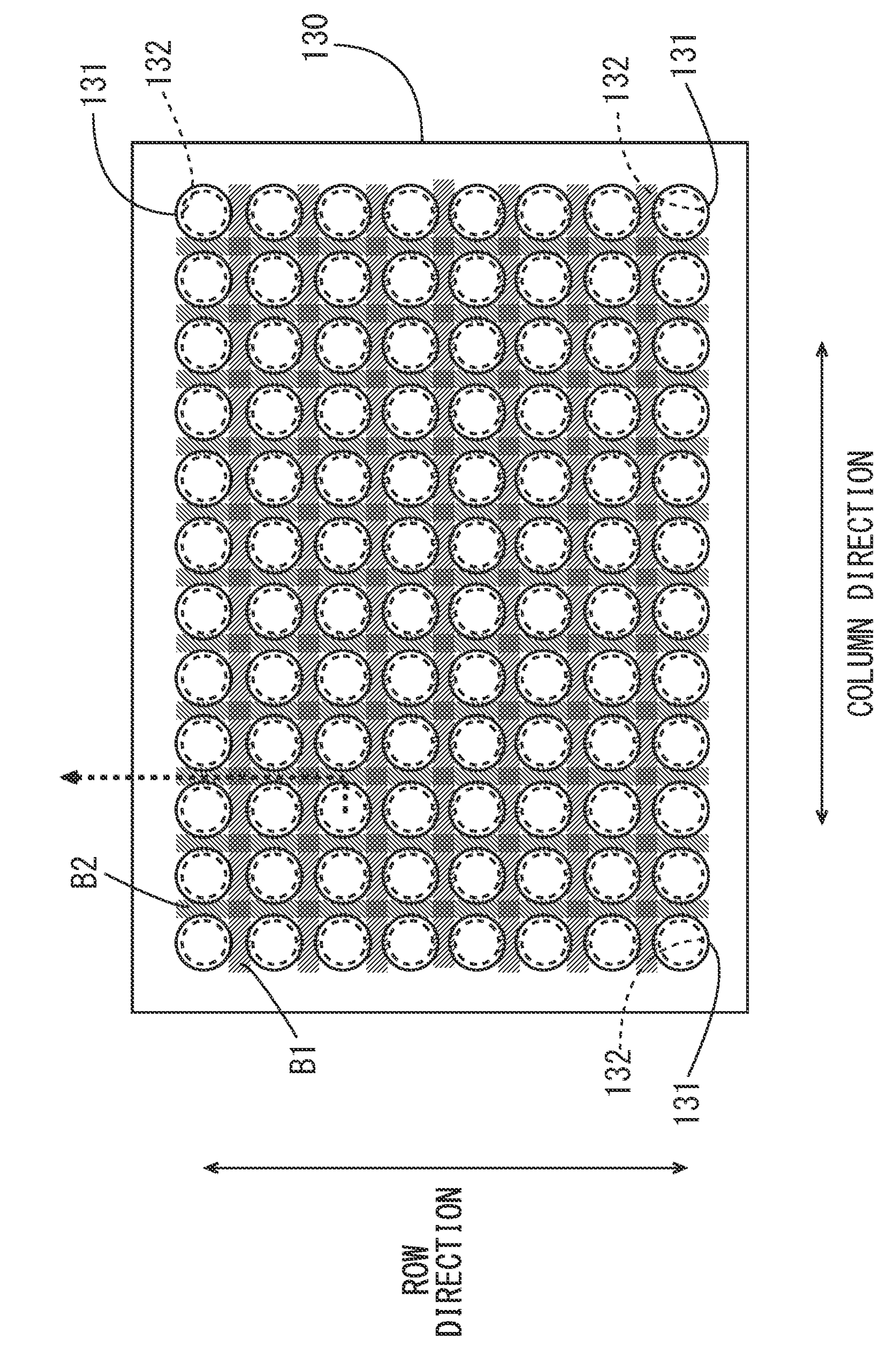
FIG. 3 is a plan view showing the configuration of a rack.

FIG. 3 is a plan view showing the configuration of the rack 130. As shown in FIG. 3, the rack 130 has a rectangular shape in a plan view. Hereinafter, the short-side direction of the rectangular rack 130 is referred to as a row direction, and the long-side direction of the rectangular rack 130 is referred to as a column direction. The short-side direction or the row direction is an example of a first direction, and the long-side direction or the column direction is an example of a second direction.

In the rack 130, 96 holes 132 arranged in 8 rows by 12 columns are provided. Thus, a strip-shaped region B1 extending in the column direction between two holes 132 adjacent to each other in the column direction is defined. Further, a strip-shaped region B2 extending in the row direction between two holes 132 adjacent to each other in the column direction is defined. A replacement tip 131 is held by each hole 132.

Figure 4:
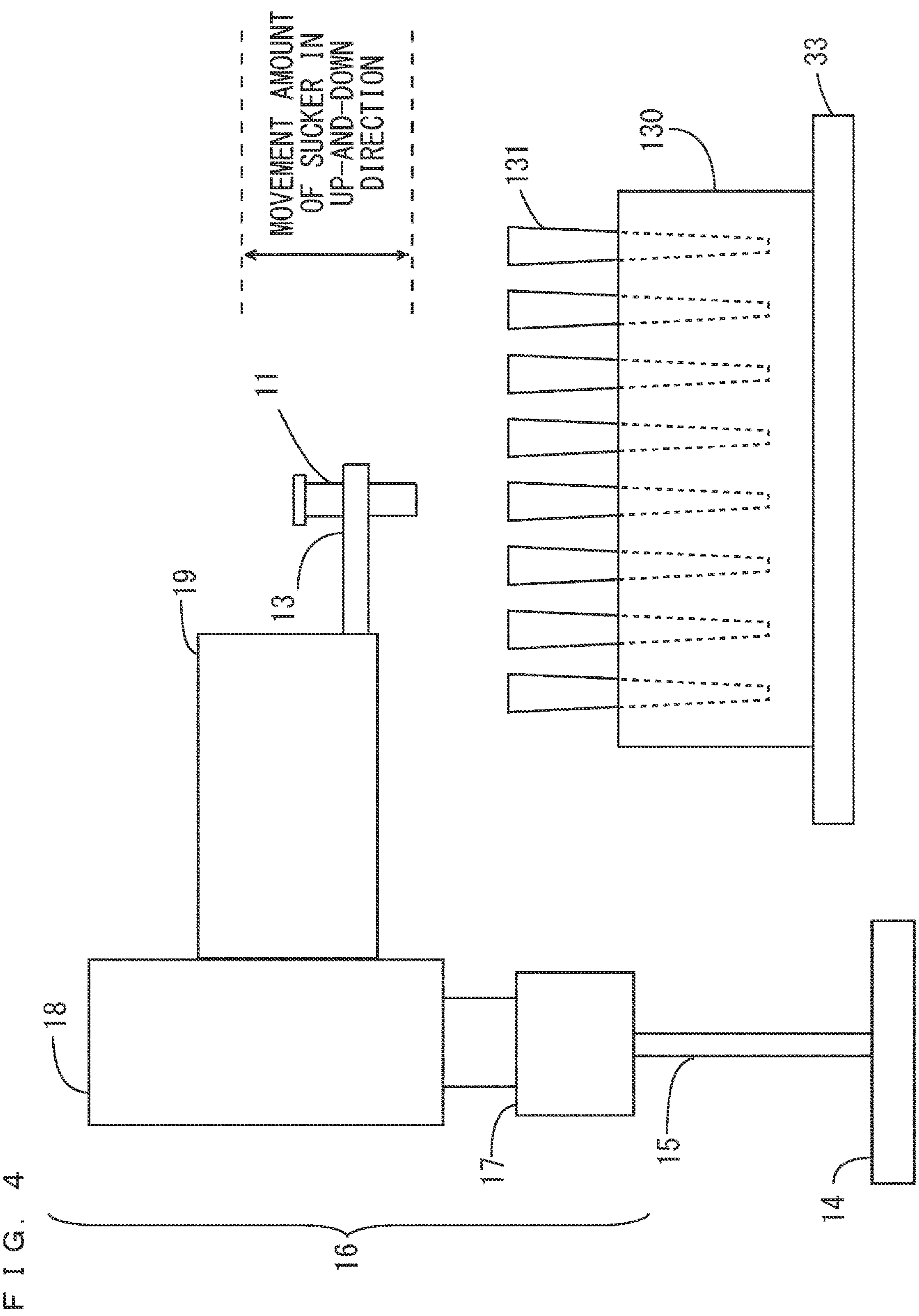
FIG. 4 is a diagram for explaining attachment of a tip to a sucker and movement of the sucker.
Figure 5:
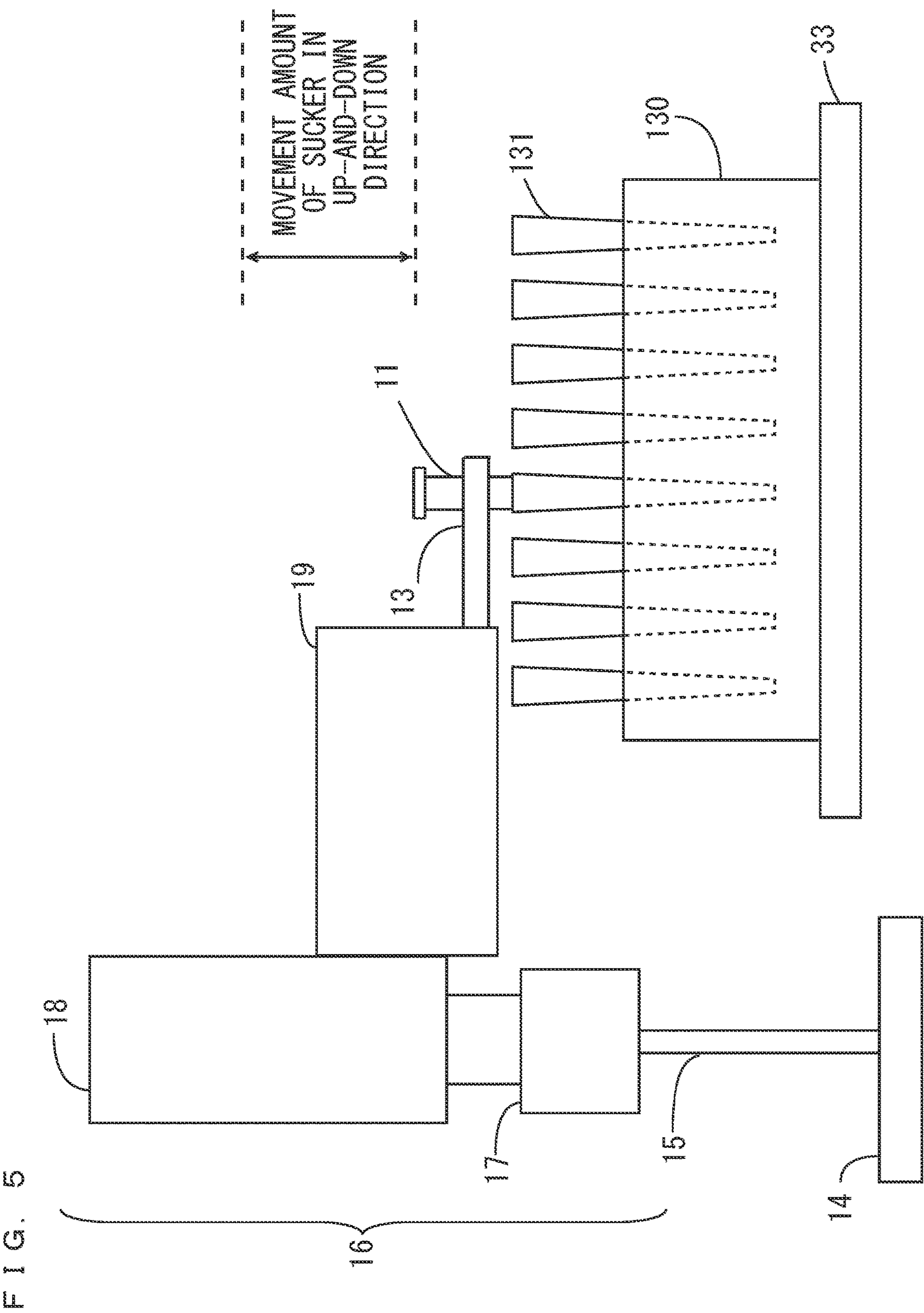
FIG. 5 is a diagram for explaining the attachment of the tip to the sucker and the movement of the sucker.

FIGS. 4 to 7 are diagrams for explaining the attachment of the tip 12 to the sucker 11 and the movement of the sucker 11. As shown in FIG. 4, when the tip 12 is attached to the sucker 11, the sucker 11 moves such that the end of the sucker 11 is located above any replacement tip 131 out of the plurality of replacement tips 131 held by the rack 130. Next, as shown in FIG. 5, the sucker 11 is lowered, so that the above-mentioned replacement tip 131 is attached to the end of the sucker 11 as a tip 12. Subsequently, as shown in FIG. 6, the sucker 11 is lifted.

Thereafter, as shown in FIG. 7, with the lower end of the tip 12 attached to the sucker 11 located farther downwardly than the upper end of another replacement tip 131 held by the rack 130, the sucker 11 moves horizontally to a position outwardly of the rack 130 from above the rack 130. Here, in regard to the movement of the sucker 11 to which the tip 12 is being attached, the sucker 11 passes along the region between a plurality of holes 132 and above the region between the plurality of holes 132 of the rack 130. In the present example, as indicated by the thick dotted arrow in FIG. 3, the sucker 11 passes along the strip-shaped region B2 and above the strip-shaped region B2. The sucker 11 may pass along not the strip-shaped region B2 but the strip-shaped region B1, and above the strip-shaped region B1.

With this configuration, although the lower end of the tip 12 attached to the sucker 11 is located farther downwardly than the upper end of another replacement tip 131 held by the rack 130, it is possible to move the sucker 11 from above the rack 130 to a position outwardly of the rack 130 with simple control without collision of the tip 12 attached to the sucker 11 with another replacement tip 131 held by the rack 130. Further, since the moving distance of the sucker 11 in the up-and-down direction is short, the sucker 11 can move from above the rack 130 to a position outwardly of the rack 130 more quickly.

The sucker 11 and the rack 130 may be moved relative to each other in a horizontal plane. Therefore, the rack 130 may be moved without movement of the sucker 11 in the horizontal plane. In the present example, the rack 130 is moved in the horizontal plane by the mover 36 of FIG. 1.

(4) Reference Example and Comparative Example

Figure 8:
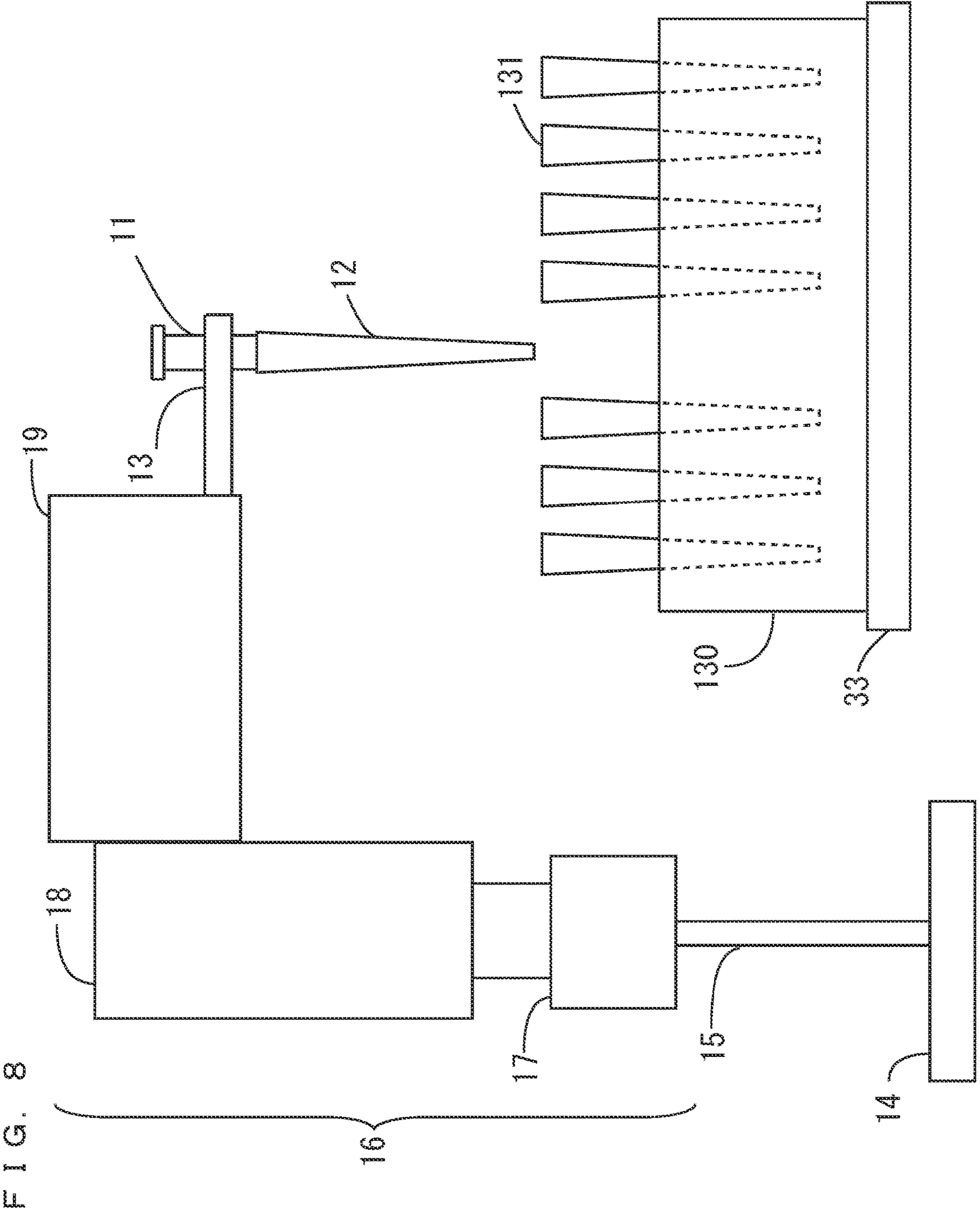
FIG. 8 is a diagram for explaining movement of the sucker in a reference example.
Figure 9:
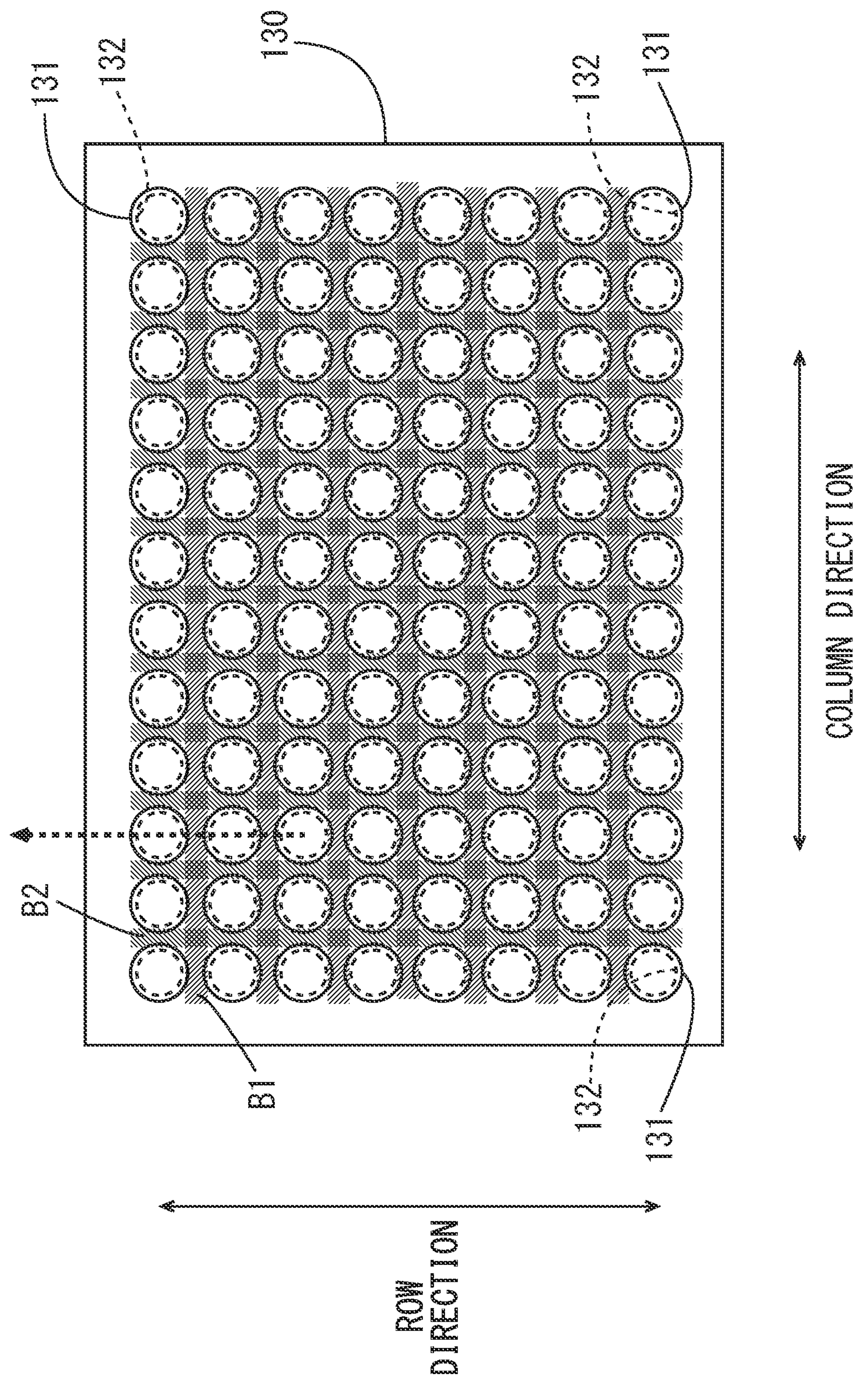
FIG. 9 is a plan view for explaining the movement of the sucker in the reference example.
Figure 10:
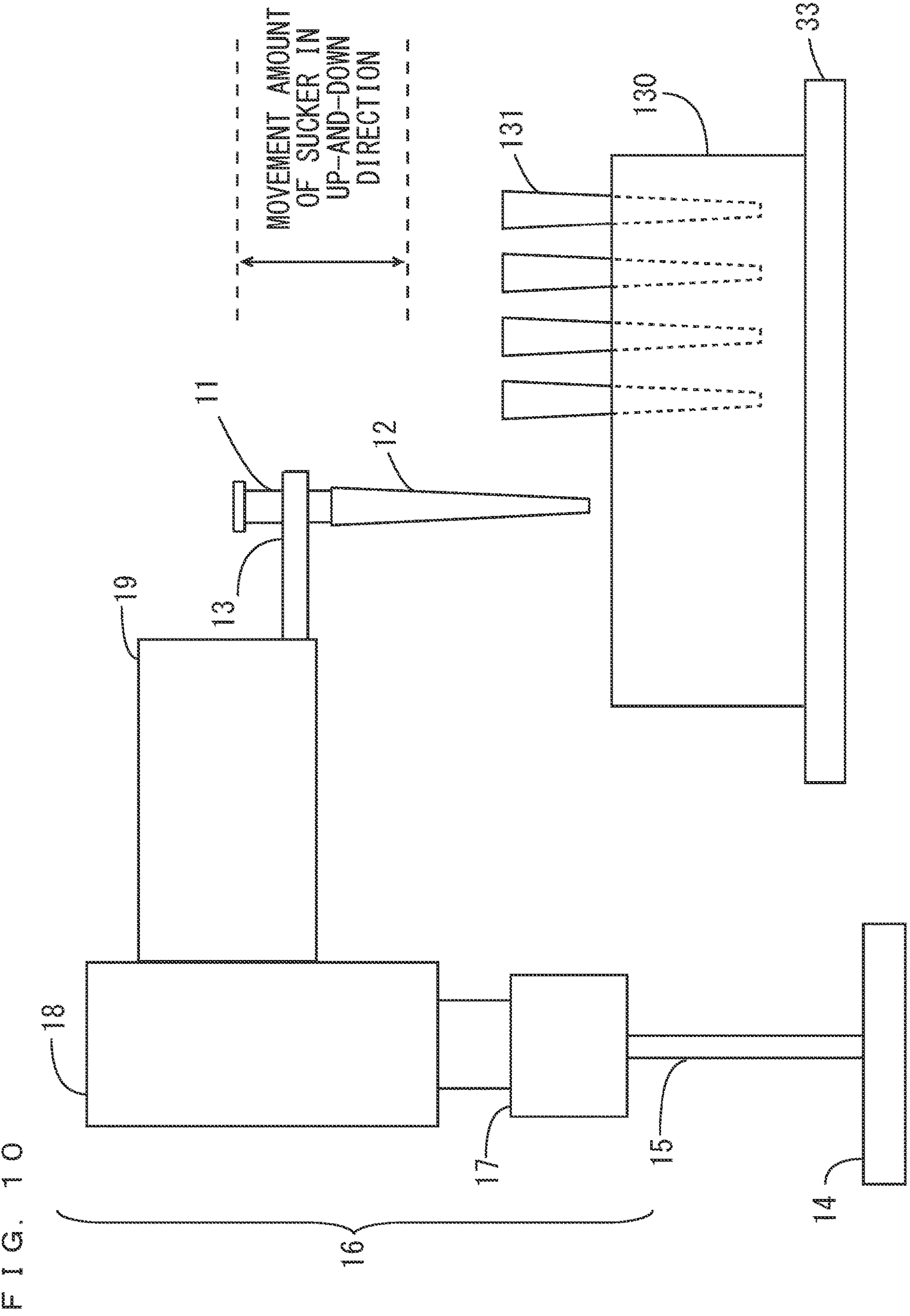
FIG. 10 is a diagram for explaining movement of the sucker in a comparative example.
Figure 11:
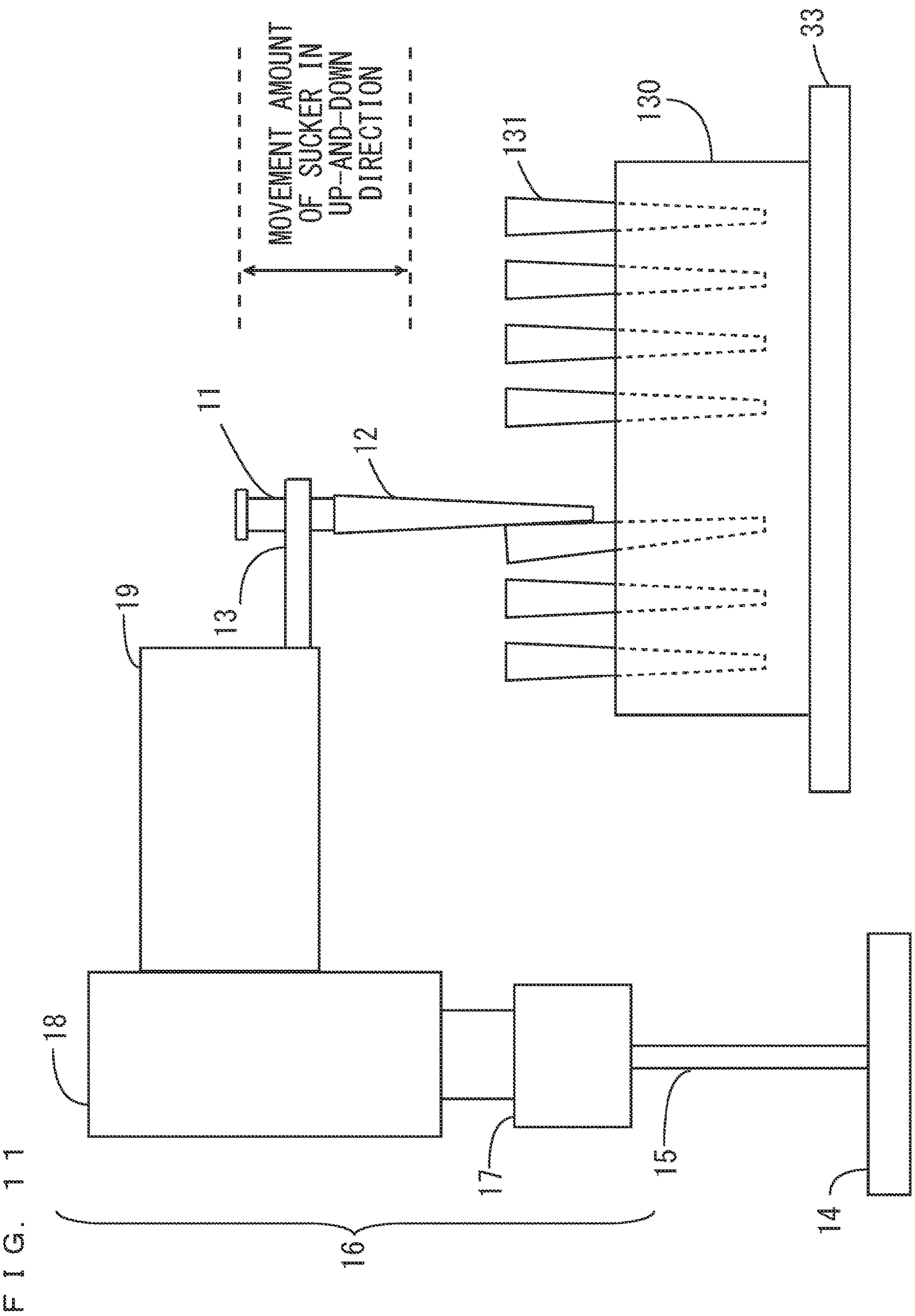
FIG. 11 is a diagram for explaining the movement of the sucker in the comparative example.

FIGS. 8 and 9 are diagrams for explaining the movement of the sucker 11 in a reference example. FIGS. 10 and 11 are diagrams for explaining the movement of the sucker 11 in a comparative example. In the reference example of FIG. 8, the movement amount of the sucker 11 in the up-and-down direction is sufficiently large. In this case, as shown in FIG. 8, the sucker 11 can be lifted such that the end of the tip 12 attached to the sucker 11 is located farther upwardly than the upper ends of the replacement tips 131 held by the rack 130.

Therefore, in the reference example, the sucker 11 does not have to pass along the region between a plurality of holes 132 and above the region between the plurality of holes 132 of the rack 130 with the tip 12 attached. That is, as indicated by the thick dotted line in FIG. 9, the sucker 11 may pass above holes 132 to cross the holes 132 of the rack 130 with the tip 12 attached. Also in this case, it is possible to move the sucker 11 from above the rack 130 to a position outwardly of the rack 130 without collision of the tip 12 attached to the sucker 11 with another replacement tip 131 held by the rack 130.

On the other hand, the suction device 10 and the observation device 20 are sufficiently spaced apart from each other in FIG. 1 to facilitate viewing. However, in the cell picking device 100, part of the suction driver 19 of the suction device 10 is actually located below a support member (not shown) for supporting the illuminator 22 of the observation device 20. Therefore, the movement amount of the sucker 11 in the up-and-down direction is limited so as to prevent interference of the suction driver 19 with the above-mentioned support member. Specifically, the movement amount of the sucker 11 in the up-and-down direction is smaller than the length of the tip 12 in an axial direction.

With the above-mentioned limitation, similarly to the reference example, the sucker 11 to which the tip 12 is being attached moves above any holes 132 to cross the holes 132 in the comparative example. Also with this configuration, in a case where replacement tips 131 are not held by the holes 132, the tip 12 does not collide with a replacement tip 131 as shown in FIG. 10. However, in a case where the replacement tips 131 are held by the holes 132, the tip 12 collides with a replacement tip 131 as shown in FIG. 11.

(5) Cell Sucking Operation

Figure 12:
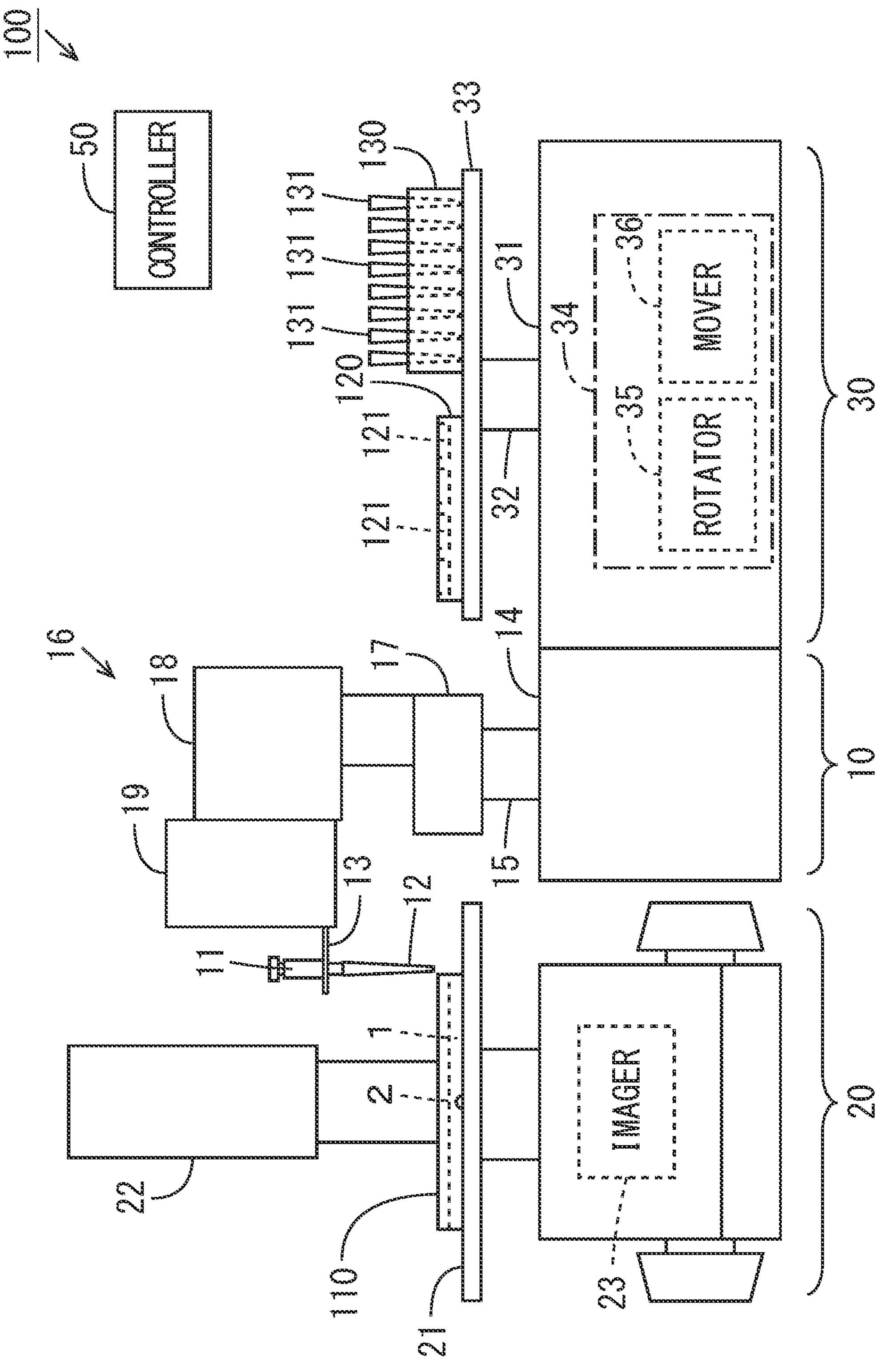
FIG. 12 is a diagram for explaining a cell sucking operation performed by the suction device.

FIG. 12 is a diagram for explaining the cell sucking operation of the suction device. As shown in FIG. 12, a predetermined volume of a liquid sample 1 is accommodated in the sample container 110 placed on the stage 21. Cells 2 to be sucked are included in the sample 1. The cells 2 are adsorbed to the bottom surface of the sample container 110 at a substantially center portion of the sample container 110. In FIG. 12, the microscope 24 is not shown.

During the cell sucking operation, the rotator 17 is rotated in a horizontal plane such that the sucker 11 and the tip 12 are directed toward the observation device 20. Further, the rotator 18 is rotated in a vertical plane such that the tip 12 attached to the sucker 11 is tilted by a predetermined angle.

Next, the suction driver 19 moves toward the end of the tip 12 in the axial direction of the tip 12. Thus, the end of the tip 12 comes into contact with the cells 2. The suction mechanism of the suction driver 19 operates in this state, so that the cells 2 adsorbed to the bottom surface of the sample container 110 are sucked by the tip 12.

(6) Cell Discharging Operation

Figure 13:
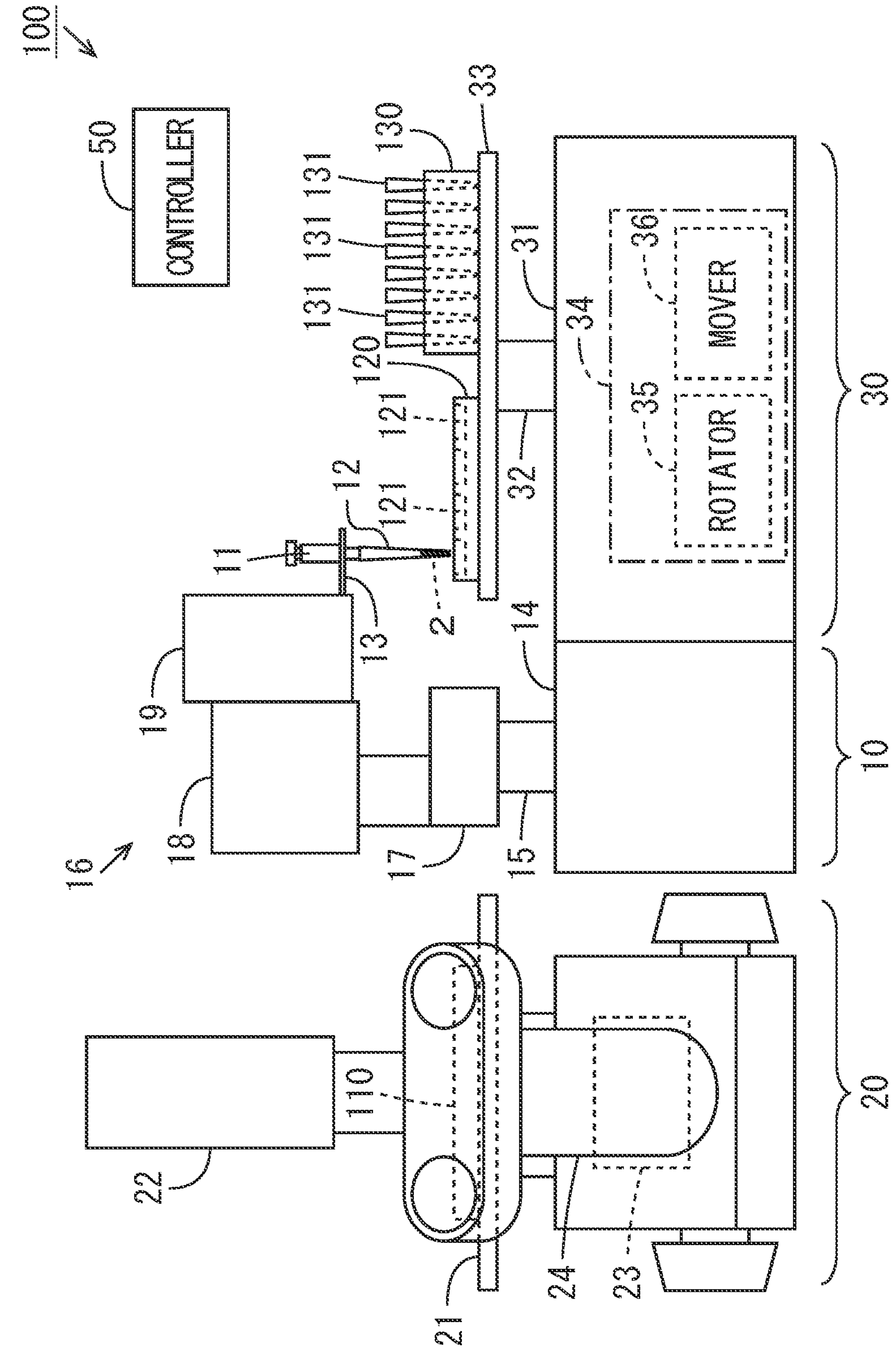
FIG. 13 is a diagram for explaining a cell discharging operation performed by the suction device.
Figure 14:
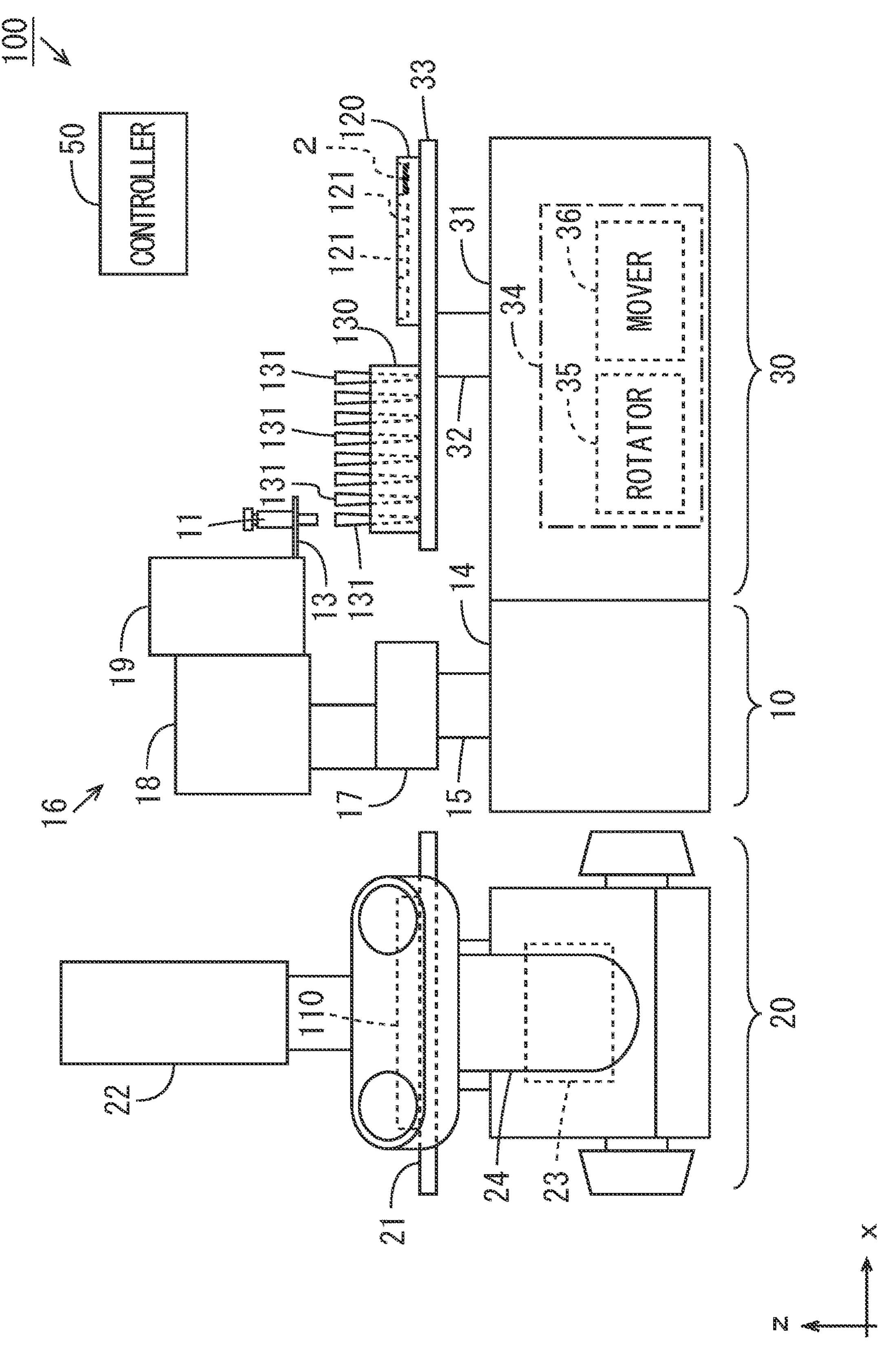
FIG. 14 is a diagram for explaining the cell discharging operation performed by the suction device.

FIGS. 13 and 14 are diagrams for explaining a cell discharging operation of the suction device 10. As shown in FIG. 13, during the cell discharging operation, the rotator 17 is rotated in a horizontal plane such that the sucker 11 and the tip 12 are directed toward the plate changer 30. Further, the rotator 35 is rotated in a horizontal plane such that the culture plate 120 is located closer to the suction device 10 than the rack 130. Further, the mover 36 moves in parallel with the horizontal plane such that any well 121 of the culture plate 120 is located below the tip 12 attached to the sucker 11.

In this state, the suction mechanism of the suction driver 19 operates, so that the cells 2 in the tip 12 are discharged downwardly. Thus, the discharged cell 2 are accommodated in the above-mentioned well 121 of the culture plate 120. After the cells 2 are discharged from the tip 12, the tip detaching mechanism of the suction driver 19 operates, so that the tip 12 is detached from the end of the sucker 11. The detached tip 12 is discarded to a discarder (not shown).

Thereafter, as shown in FIG. 14, the rotator 35 is rotated in a horizontal plane such that the rack 130 is located closer to the suction device 10 than the culture plate 120. Further, the mover 36 moves in parallel with a horizontal plane such that any replacement tip 131 held by the rack 130 is located below the end of the sucker 11. In this state, the suction driver 19 moves downwardly. In this case, the above-mentioned replacement tip 131 held by the rack 130 can be attached to the end of the sucker 11 as the tip 12. Thereafter, the tip 12 is moved to a position outwardly of the rack 130 as described above. Thus, the operation of sucking the cells 2 in FIG. 12 can be repeated.

The order of use of the wells 121 for accommodating the cells 2 in the culture plate 120 is registered in advance in the controller 50. Similarly, in the rack 130, the order of attachment of the replacement tips 131 to the sucker 11 is registered in advance in the controller 50. In a case where the operation of sucking the cells 2 is repeated, the operation of discharging the cells 2 is repeated with use of a new replacement tip 131 and a new well 121 in accordance with the order in regard to the wells 121 and the order in regard to the replacement tips 131 registered in the controller 50. Thus, the cells 2 can be accommodated in the plurality of wells 121 of the culture plate 120 automatically and in a chronological order.

(7) Cell Accommodating Process

FIG. 15 is a diagram showing the configuration of the controller of FIG. 1. FIG. 16 is a flowchart showing one example of the algorithm of a cell accommodating process executed by the controller 50. As shown in FIG. 15, the controller 50 includes an information acquirer 51, a suction processor 60 and a discharge processor 70 as functions. The functions of the controller 50 are implemented by execution of a cell accommodating program stored in a memory by the CPU of the controller 50. Part or all of the functions of the controller 50 may be implemented by hardware such as an electronic circuit. The cell accommodating process will be described below with reference to the controller 50 of FIG. 15 and the flowchart of FIG. 16.

First, the information acquirer 51 acquires various information (hereinafter referred to as registration information) registered by the user (step S1). The user can register a position at which the cells 2 are likely to be present in the sample container 110 or a position close to the position as a suction position. Further, the user can register the selection of "moving to a discharge position right after picking" or "not moving to the discharge position right after picking."

Further, the user can register the information relating to the sample container 110, the culture plate 120 and the rack 130. The information relating to the sample container 110 includes a dimension of the depth of the sample container 110, etc. The information relating to the culture plate 120 includes the number of wells 121 and the order of use of the wells 121 for accommodating the cells 2. The information relating to the rack 130 includes the number of held replacement tips 131 and the order of attachment of the replacement tips 131 to the sucker 11.

Next, the suction processor 60 executes a cell sucking process (step S2). The cell sucking process is a process of sucking the cells 2 from the sample 1 accommodated in the sample container 110 into the tip 12 based on the registration information acquired in the step S1. Although the tip 12 is attached to the sucker 11 in an initial state in the present example, in a case where the tip 12 is not attached to the sucker 11 in the initial state, the steps S24 to S26 of FIG. 18, described below, are performed between the step S1 and the step S2.

Subsequently, the discharge processor 70 executes a cell discharging process (step S3). The cell discharging process is a process of discharging the cells 2 sucked into the tip 12 in the cell sucking process of the step S2 into any well 121 of the culture plate 120 and then replacing the tip 12. Details of the cell sucking process and the cell discharging process will be described below. After the cell discharging process, the cell accommodating process ends.

(8) Cell Sucking Process

FIG. 17 is a flowchart showing one example of the algorithm of the cell sucking process of FIG. 16 executed by the suction processor 60. As shown in FIG. 15, the suction processor 60 includes an advancer 61, a suction controller 63 and a retractor 64 as further functions. The cell sucking process will be described below with reference to the sucker 11 of FIG. 12, the suction processor 60 of FIG. 15 and the flowchart of FIG. 17.

First, the advancer 61 causes the end of the tip 12 attached to the sucker 11 to advance to a position (the suction position registered in the step S1) of the sample 1 in the sample container 110 by controlling the rotators 17, 18 and the suction driver 19 (FIGS. 12 and 4, and the step S11).

Further, the suction controller 63 sucks the cells 2 into the tip 12 by controlling the suction driver 19 (step S12).

Thereafter, the suction controller 63 determines whether to continue suction (step S13). In a case where successive suction is not carried out, the suction controller 63 determines not to continue suction and proceeds to the step S14. In a case where successive suction is carried out, the suction controller 63 determines to continue suction and returns to the step S12. In a case where succession suction is repeated, the end of the tip 12 may be slightly moved.

In the step S14, the retractor 64 retracts the tip 12 from the sample 1 by controlling the suction driver 19 (step S14). In a case where the tip 12 retracts, the retractor 64 ends the cell sucking process.

(9) Cell Discharging Process

Figure 18:
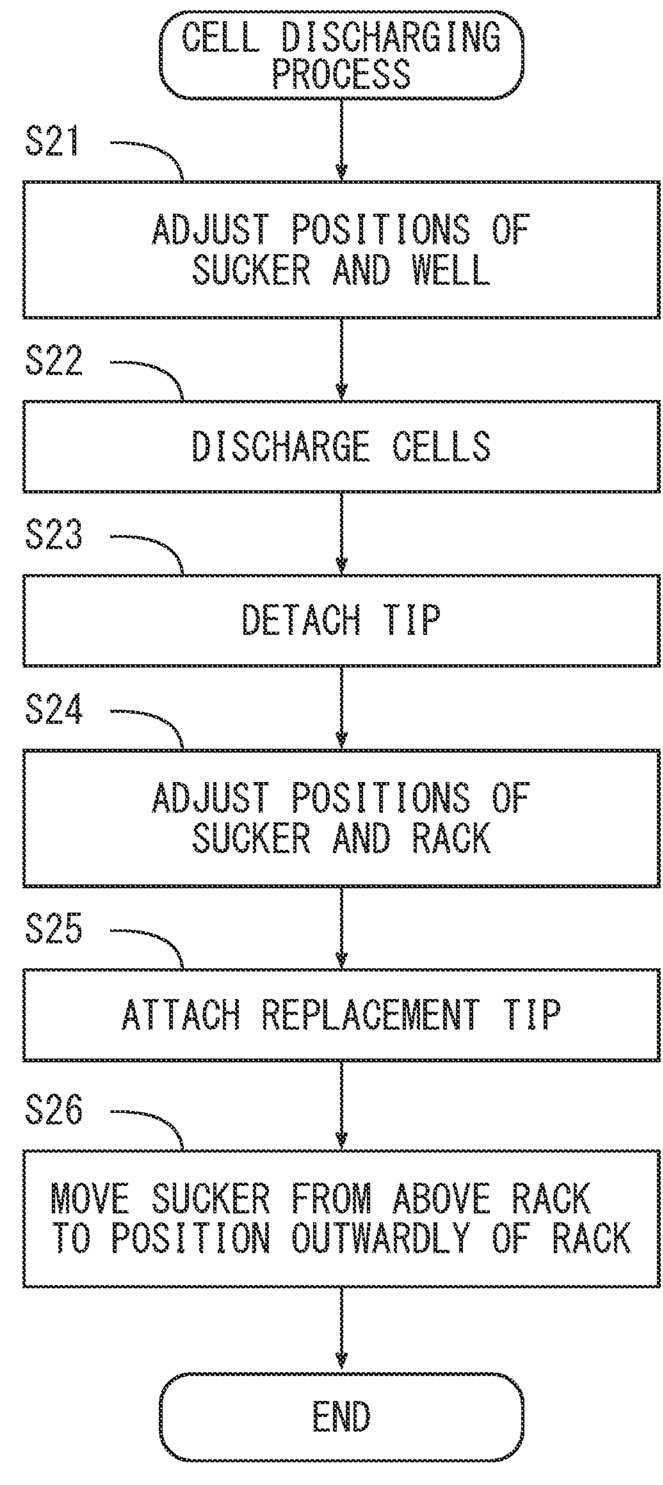
FIG. 18 is a flowchart showing one example of the algorithm of a cell discharging process of FIG. 16 executed by a discharge processor.

FIG. 18 is a flowchart showing one example of the algorithm of the cell discharging process of FIG. 16 executed by the discharge processor 70. As shown in FIG. 15, the discharge processor 70 includes a first position adjuster 71, a discharge controller 72, a detacher 73, a second position adjuster 74 and an attacher 75 as further functions. The cell discharging process will be described below with reference to the sucker 11 of FIGS. 13 and 14, the discharge processor 70 of FIG. 15 and the flowchart of FIG. 18.

First, the first position adjuster 71 adjusts the positional relationship between the sucker 11 and the culture plate 120 by controlling the rotators 17, 18, 35 and the mover 36 in accordance with the order in regard to the wells 121 acquired in the step S1 (FIG. 13 and the step S21). In this case, a well 121 in which the cells 2 are to be accommodated next in the culture plate 120 is located below the end of the sucker 11.

Next, the discharge controller 72 discharges the cells 2 into the tip 12 by controlling the suction driver 19 (step S22). Thus, the cells 2 are accommodated in the above-mentioned well 121. Subsequently, the detacher 73 detaches the tip 12 from the sucker 11 by controlling the suction driver 19 (step S23).

In the step S24, the second position adjuster 74 adjusts the positional relationship between the sucker 11 and the rack 130 by controlling the rotators 17, 18, 35 and the mover 36 in accordance with the order in regard to the replacement tips 131 acquired in the step S1 (FIG. 14 and the step S24). In this case, a replacement tip 131 to be attached to the sucker 11 next in the rack 130 is located below the end of the sucker 11.

Next, the attacher 75 attaches the above-mentioned replacement tip 131 to the sucker 11 by controlling the suction driver 19 (step S25). Specifically, the replacement tip 131 is attached to the sucker 11 as a tip 12 by downward movement of the sucker 11.

Next, the movement controller 76 moves the sucker 11 to a position outwardly of the rack 130 from above the rack 130 by controlling the rotators 17, 18, 35 and the mover 36. At this time, the sucker 11 passes along the region between a plurality of holes 132 and above the region between the plurality of holes 132 of the rack 130 (FIG. 14 and the step S26). In a case where the sucker 11 moves to a position outwardly of the rack 130, the movement controller 76 ends the cell discharging process.

(10) Effects

In this cell picking device 110, in regard to the movement of the sucker 11 to which the tip 12 is being attached, the sucker 11 passes along the strip-shaped region B1 or B2, and above the strip-shaped region B1 or B2.

With this configuration, even in a case where movement of the sucker 11 in the up-and-down direction is limited, the tip 12 attached to the sucker 11 does not collide with another replacement tip 13 held by the rack 130. Thus, the sucker 11 can be moved to a position outwardly of the rack 130 from above the rack 130 with simple control.

Further, because it is not necessary for the sucker 11 to be moved largely in the up-and-down direction, the sucker 11 can be moved from above the rack 130 to a position outwardly of the rack 130 in a short period of time. Further, the size of the cell picking device 100 can be reduced in the up-and-down direction.

Further, because the movement amount of the sucker 11 in the up-and-down direction can be limited, the observation device 20 can be provided easily to be adjacent to the suction device 10 without interfering with the suction device 10. Therefore, the user can magnify and observe a sample using the observation device 20.

(11) Other Embodiments (a) While the sucker 11 is not configured to be movable in parallel with a horizontal plane in the above-mentioned embodiment, the embodiment is not limited to this. The sucker 11 may be configured to be movable in parallel with a horizontal plane. Specifically, a mover similar to the mover 36 may be provided in the suction device 10. In this case, the first position adjuster 71 or the second position adjuster 74 may control the mover of the suction device 10 instead of the mover 36. Further, the mover 36 does not have to be provided in the plate changer 30.

(b) While the driver 34 includes the rotator 35 in the above-mentioned embodiment, the embodiment is not limited to this. In a case where the culture plate 120 and the rack 130 can be selectively moved to the vicinity of the suction device 10 by sufficiently large movement of the supporter 33 by the mover 36 in a horizontal plane, the driver 34 does not have to include the rotator 35.

(12) Aspects

It is understood by those skilled in the art that the plurality of above-mentioned illustrative embodiments are specific examples of the below-mentioned aspects.

(Item 1) A cell picking device according to one aspect may include a supporter that supports a rack having a plurality of holes for holding a plurality of pipette tips, a sucker used to suck a sample, a driver that moves the sucker in an up-and-down direction and moves the sucker and the supporter relative to each other in a horizontal direction, and a controller that controls the driver such that, any pipette tip out of the plurality of pipette tips held by the rack is attached to the sucker by movement of the sucker in the up-and-down direction and the sucker is moved to a position outwardly of the rack by movement of the sucker and the supporter relative to each other, wherein the controller may control the driver such that the sucker moves along a region between the plurality of holes and above the region between the plurality of holes of the rack to a position outwardly of the rack from above the rack with a lower end of a pipette tip attached to the sucker located farther downwardly than an upper end of another pipette tip held by the rack.

In this cell picking device, in regard to the movement of the sucker to which the tip is being attached, the sucker passes along the region between a plurality of holes and above the region between the plurality of holes of the rack.

With this configuration, even in a case where the movement amount of the sucker in the up-and-down direction is limited, the sucker can be moved to a position outwardly of the rack from above the rack without collision of the tip attached to the sucker with another replacement tip held by the rack.

(Item 2) The cell picking device according to item 1, wherein the plurality of holes may be formed in the rack at equal intervals in a first direction and a second direction that intersects with the first direction, a first strip-shaped region extending in the second direction may be formed between two holes adjacent to each other in the first direction of the rack, and a second strip-shaped region extending in the first direction may be formed between two holes adjacent to each other in the second direction, and the controller may control the driver such that the sucker moves along the first or second strip-shaped region and above the first or second strip-shaped region to a position outwardly of the rack.

In this case, the sucker can be moved from above the rack to a position outwardly of the rack with simple control without collision of the tip attached to the sucker with another replacement tip held by the rack.

(Item 3) The cell picking device according to item 1 or 2, may further include a suction device including the sucker, and an observation device provided to be adjacent to the suction device and used for observation of a sample.

With this configuration, because the movement amount of the sucker in the up-and-down direction can be limited, the observation device can be provided easily to be adjacent to the suction device without interfering with the suction device.

Therefore, the user can magnify and observe a sample using the observation device.

(Item 4) The cell picking device according to item 1 or 2, wherein the driver may be configured to cause the sucker to perform a sucking operation and a discharging operation in accordance with control carried out by the controller and is configured to detach the pipette tip from the sucker, and the controller may control the driver so as to sequentially carry out first control for sucking a sample from a sample container accommodating a sample to a pipette tip, second control for discharging a sample sucked by the sucker into the pipette tip into any well of a culture plate having a plurality of wells, third control for detaching the pipette tip from the sucker, and fourth control for attaching any pipette tip held by the rack to the sucker.

In this case, a sample is sucked into the pipette tip from the sample container. Thereafter, the sample is discharged into any well of the culture plate from the pipette tip. Further, the pipette tip is detached from the sucker, and any pipette tip held by the rack is attached to the sucker. Thus, the sucked cells can be accommodated in any well of the culture plate automatically.

(Item 5) The cell picking device according to item 4, wherein the controller may repeatedly carry out the first control, the second control, the third control and the fourth control such that a sample is charged into a well different from a well to which a sample has already been discharged in the second control.

In this case, a sample is sucked into the pipette tip from the sample container. Thereafter, the sample is discharged into any well of the culture plate from the pipette tip. Further, the pipette tip is detached from the sucker, and any pipette tip held by the rack is attached to the sucker. With repetition of this control, the sucked cells can be accommodated in the plurality of wells of the culture plate automatically and successively.

(Item 6) The cell picking device according to item 4, wherein the driver may be configured to be capable of rotating the supporter, the supporter may further support the culture plate, the controller may control rotation of the supporter by the driver such that the culture plate is located closer to the sucker than the rack in the second control, and the rack is located closer to the sucker than the culture plate in the fourth control.

In this case, it is possible to selectively move the culture plate and the rack to a position accessible by the sucker without increasing the moving range of the supporter.

The invention claimed is:

1. A method of operating a cell picking device, the cell picking device comprising:

a supporter that supports a rack having a plurality of holes for holding a plurality of pipette tips;

a sucker used to suck a sample;

a driver that moves the sucker in an up-and-down direction and moves the sucker and the supporter relative to each other in a horizontal direction; and a controller that controls the driver, the rack including a first strip-shaped region extending in a column direction between two holes adjacent to each other in the column direction, and a second strip-shaped region extending in a row direction between two holes adjacent to each other in the column direction, the method comprising:

moving the sucker such that a tip of the sucker is located above any pipette tip out of the plurality of pipette tips held by the rack:

attaching the pipette tip to the tip of the sucker by lowering the sucker;

raising the sucker above the rack such that a lower end of the pipette tip attached to the sucker is located farther downwardly than an upper end of another pipette tip held by the rack;

moving the sucker to a position outwardly of the rack along and above two strip-shaped regions between the plurality of holes of the rack such that the lower end of the pipette tip traces between the plurality of holes and between the plurality of pipette tips held by the rack, with the lower end of the pipette tip attached to the sucker being located farther downwardly than the upper end of the other pipette tip held by the rack; and moving the sucker from a position above the rack to a position outwardly of the rack without collision of the pipette tip attached to the sucker with the other pipette tip held by the rack.

2. The method of operating a cell picking device according to claim 1, wherein a moving amount of the sucker in an upward direction is limited such that the lower end of the pipette tip attached to the sucker is located farther downwardly than the upper end of the other pipette tip held by the rack.

3. A cell picking device comprising:

a supporter that supports a rack having a plurality of holes for holding a plurality of pipette tips, wherein the rack includes:

a first strip-shaped region extending in a column direction between two holes adjacent to each other in the column direction, and a second strip-shaped region extending in a row direction between two holes adjacent to each other in the column direction;

a sucker used to suck a sample;

a driver that moves the sucker in an up-and-down direction and moves the sucker and the supporter relative to each other in a horizontal direction; and a controller configured to control the driver such that:

any pipette tip out of the plurality of pipette tips held by the rack is attached to the sucker by movement of the sucker in the up-and-down direction;

after the pipette tip is attached to the sucker, the sucker is moved to a position outwardly of the rack by movement of the sucker and the supporter relative to each other by:

raising the sucker above the rack until a lower end of the pipette tip attached to the sucker is located farther downwardly than an upper end of another pipette tip held by the rack; and moving the sucker along and above the two strip shaped regions between the plurality of holes of the rack to a position outwardly of the rack, such that the lower end of the pipette tip traces between the plurality of holes and between the plurality of pipette tips held by the rack, with the lower end of the pipette tip attached to the sucker being located not above the upper end of the other tip held by the rack but farther downwardly than the upper end of the other pipette tip held by the rack.

4. The cell picking device according to claim 3, wherein a moving amount of the sucker in an upward direction is limited such that the lower end of the pipette tip attached to the sucker is located farther downwardly than the upper end of the other pipette tip held by the rack.

* * * * *